United States Patent [19]

Tsao

[11] Patent Number: 6,001,642
[45] Date of Patent: Dec. 14, 1999

[54] BIOREACTOR AND CELL CULTURING PROCESSES USING THE BIOREACTOR

[75] Inventor: Yow-Min D. Tsao, Friendswood, Tex.

[73] Assignee: Wyle Laboratories, Inc. Life Sciences, Houston, Tex.

[21] Appl. No.: 09/106,987

[22] Filed: Jun. 29, 1998

[51] Int. Cl.[6] ................................................. C12M 3/02
[52] U.S. Cl. ................................. 435/297.3; 435/298.2; 435/394; 435/403
[58] Field of Search ..................................... 435/383, 394, 435/395, 403, 297.2, 297.3, 297.5, 298.2

[56] References Cited

U.S. PATENT DOCUMENTS

| | | |
|---|---|---|
| 3,827,943 | 8/1974 | Mann . |
| 3,925,165 | 12/1975 | Müller . |
| 4,244,916 | 1/1981 | Guigan . |
| 4,343,904 | 8/1982 | Birch et al. . |
| 4,535,062 | 8/1985 | Müller . |
| 4,846,786 | 7/1989 | Freed et al. . |
| 4,988,623 | 1/1991 | Schwarz et al. . |
| 5,010,014 | 4/1991 | Gebhardt . |
| 5,026,650 | 6/1991 | Schwartz . |
| 5,151,368 | 9/1992 | Brimhall et al. . |
| 5,153,131 | 10/1992 | Wolf et al. . |
| 5,153,132 | 10/1992 | Goodwin et al. . |
| 5,153,133 | 10/1992 | Schwarz et al. . |
| 5,155,034 | 10/1992 | Wolf et al. . |
| 5,155,035 | 10/1992 | Schwarz et al. . |
| 5,330,908 | 7/1994 | Spaulding . |
| 5,437,998 | 8/1995 | Schwarz et al. . |
| 5,523,228 | 6/1996 | Ingram et al. ........................ 435/298.2 |
| 5,565,361 | 10/1996 | Mutsakis et al. . |
| 5,605,835 | 2/1997 | Hu et al. . |
| 5,622,857 | 4/1997 | Goffe . |
| 5,665,594 | 9/1997 | Schwarz et al. . |
| 5,686,301 | 11/1997 | Falkenberg et al. . |
| 5,688,687 | 11/1997 | Palsson et al. . |
| 5,702,941 | 12/1997 | Schwarz . |
| 5,763,279 | 6/1998 | Schwarz et al. . |

OTHER PUBLICATIONS

Stathopoulos et al., *Biotechnol. Bioeng.*, 27:1021–1026 (1985).
Croughan et al., *Biotechnol. Bioeng.*, 29:130–141 (1987).
Croughan et al., *Biotechnol. Bioeng.*, 33:731–744 (1989).
Tsao et al., "Fluid Dynamics Within a Rotating Bioreactor in Space and Earth Environments", *Journal of Spacecraft and Rockets*, 31:937–943 (1994).
Tsao et al., "Mass Transfer Characteristics of NASA Bioreactors by Numerical Simulation", *Advances in Heat and Mass Transfer in Biotechnology*(Clegg, S., ed.) HTD–vol. 355:69–73 (1997).
Hung, R.J. et al., "Time Sequence Evolution of Human Cell Deformation in Micro– and Hypergravity", *Microgravity Quarterly* 5:91–99 (1995).
Tsao, Y.D. et al., "Responses of Gravity Level Variations on the NASA/JSC Bioreactor System", *The Physiologist* 35:S–49—S–50 (1992).
Moroz, Pavel E., "The Cell in the Field of Gravity and the Centrifugal Field", *J. theor. Biol.* 107:303–320 (1984).
Schatz, A. et al., "Effects of Combined O–G Simulation and Hypergravity on Eggs of the Nematode, *Ascaris suum*", *Aerospace Medicine* 43:614–619 (1972).

*Primary Examiner*—William H. Beisner
*Attorney, Agent, or Firm*—Arnold, White & Durkee

[57] ABSTRACT

A bioreactor and cell culturing method using the bioreactor have been developed to enhance cell production and growth and decrease the shear forces on the cells and multicellular aggregates. The bioreactor contains a dome-shaped culture vessel having walls defining an interior volume, an apex, a bottom circular edge, and a axis of symmetry perpendicular to the bottom circular edge; and a gas-permeable membrane fluidtightly integrated with the bottom circular edge of the culture vessel. The bioreactor may further contain a rotating base fluidtightly integrated with the gas-permeable membrane, wherein the rotating base is fixed to rotate about the axis of symmetry of the dome-shaped culture vessel set on a substantially horizontal axis.

18 Claims, 3 Drawing Sheets

BIOREACTOR AND CELL CULTURING PROCESSES USING THE BIOREACTOR

FIELD OF THE INVENTION

The invention relates to a bioreactor and a method for culturing cells using the bioreactor. More particularly, the invention is directed to a bioreactor having a dome-shaped culture vessel that rotates about its axis of symmetry set on a substantially horizontal plane and a method for culturing cells in that bioreactor.

BACKGROUND OF THE INVENTION

Many academic and industrial processes rely on in vitro culturing to generate greater amounts of cells of interest. In these processes, a sample of cells is generally placed in a vessel, provided with nutrients, and agitated. After a sufficient period of time to allow production and growth of new cells, the cultured cells are removed from the vessel and purified. For example, small-scale cell culturing has traditionally been performed in shallow shaker flasks. The cells and nutrient media are combined in the flask and a mechanical or magnetic stirring mechanism circulates the mixture. This circulation is important to prevent the cells from settling to the bottom of the culture vessel due to gravity and to ensure sufficient nutrient transfer to and waste bioproducts from the growing cells.

These mass transfer requirements are important for all forms of culturing cells, for example, in the form of a single cells, multicellular aggregates or cells attached to a substrate. In many culture systems, particularly mammalian culture systems, the formation of multicellular aggregates is important to accumulate large biomasses. Mammalian cells are also often cultured in an attached state to mimic the in vivo environment. When shear forces become too high, these forces can deform and damage individual cells, impede cell growth, prevent or limit the aggregation of cells, or pull apart aggregates and tear the walls of adjacent cells.

Several research groups have studied the effects of shear stress on cell cultures. Stathopoulos et al., *Biotechnol. Bioeng.* 27:1021–1026 (1985), studied shear stress effects on human embryonic kidney cells in vitro and reported that forces of 0.65 N/m$^2$ had significant effects on cell morphology and forces higher than 2.6 N/M$^2$ caused marked reduction in cell viability. Croughan et al., *Biotechnol. Bioeng.*, 29:130–141 (1987), and Croughan et al., *Biotechnol Bioeng.* 33:731–744 (1989), evaluated growth of FS-4 (human diploid fibroblasts) microcarrier cultures at various impeller rotation rates in spinner vessels equipped with magnetic stir bars. Croughan et al. (1987) suggests that this analysis would not apply to vessels having different geometries.

A variety of geometries have been proposed for cell culture vessels. Tsao et al., "Fluid Dynamics Within a Rotating Bioreactor in Space and Earth Environments," *Journal of Spacecraft and Rockets* 31:937–943 (1994), and Tsao et al., "Mass Transfer Characteristics of NASA Bioreactors by Numerical Simulation," *Advances in Heat and Mass Transfer in Biotechnology* (Clegg, S., ed.) HTD-Vol. 355:69–73 (1997), disclose a bioreactor having a culturing vessel with two concentric, independently rotating cylinders. U.S. Pat. Nos. 5,026,650 (Schwartz., issued Jun. 25, 1991); 5,155,034 (Wolf et al., issued Oct. 13, 1992); and 5,153,133 (Schwartz et al., issued Oct. 6, 1992) disclose a bioreactor having a horizontally disposed cylindrical culture vessel that rotates about its longitudinal axis. The vessel contains a coaxially-disposed, oxygen-permeable membrane and access ports to inject or withdraw nutrient media.

U.S. Pat. No. 5,151,368 (Brimhall et al., issued Sep. 29, 1992) describes a dual-axis continuous flow bioreactor for handling high solids loaded materials such as coal and mineral ores. The bioreactor is mounted to a horizontal axle, corresponding to the bioreactor's longitudinal axis, and moves in a circular path about its vertical shaft while simultaneously rotating about its horizontal axis by an interlocking set of bevel ring gears. The vessel contains several conduits for introducing and withdrawing media and gases.

U.S. Pat. No. 5,565,361 (Mutsakis et al., issued Oct. 15, 1996) describes a bioreactor containing a porous, fibrous sheet material that acts as a motionless mixing element and as a substrate for attaching the cultivating cells. U.S. Pat. No. 5,622,857 (Goffe, issued Apr. 22, 1997) describes a bundled hollow fiber bioreactor and its use to prepare eucaryotic cells. The flow of oxygenated nutrient medium is maintained at a sufficient pressure to prevent the formation of bubbles that may block flow of media through the fibers. U.S. Pat. No. 5,688,687 (Palsson et al., issued Nov. 18, 1997) describes a bioreactor for mammalian cell growth having a circular cell growth chamber between a planar cell bed and a gas permeable membrane. Media inlet and outlets are arranged in a concentric circular arrangement and provide for the delivery of nutrients to the cells. U.S. Pat. No. 5,605,835 (Hu et al., issued Feb. 25, 1997) describes a bioreactor that immobilizes animal cells in an insoluble, biocompatible matrix. Selective membranes allow for the separation of cell nutrients and cell wastes while collecting the desired cell products within the cell chamber.

There is a need for improved bioreactors and cell culturing methods that enhance the production and growth of cells without creating shear forces that damage cultivating cells or multicellular aggregates.

SUMMARY OF THE INVENTION

This invention relates to a bioreactor and a cell culturing method that use the bioreactor. More particularly, the invention is directed to a bioreactor having a dome-shaped culture vessel that rotates about its axis of symmetry set on a substantially horizontal plane and a method for culturing cells in that bioreactor.

The inventive bioreactor comprises a dome-shaped culture chamber having walls defining an interior volume and a circular ridge at the bottom of the chamber. The circular ridge of the culture chamber is fluidtightly integrated with a gas permeable membrane. The membrane side of the culture chamber may be fluidtightly integrated with a rotating base in an orientation where the axis of symmetry of the dome-shaped culture chamber is substantially horizontal. The dome-shaped design and horizontal orientation provide a low shear environment and mass transfer that is favorable for culturing cells, particularly mammalian cells that form multicellular aggregates for the production of large biomasses.

The method according to the invention comprises providing the inventive bioreactor, adding cells and appropriate nutrients to the interior volume of the dome-shaped culture chamber, and rotating the base at a rate that generates suitable mass transfer and low shear stress.

In a preferred embodiment, the bioreactor comprises additional features that permit efficient addition of cell samples and removal of cell product, efficient addition and removal of nutrients and gases, easy assembly of the bioreactor components, and a flexible design to allow for a wide variety of cell cultures and culturing conditions.

BRIEF DESCRIPTION OF THE DRAWINGS

The following figures form part of the specification and are included to further demonstrate certain aspects of the present invention. The invention may be better understood by reference to one or more of these drawings in combination with the detailed description of specific embodiments presented herein.

DETAILED DESCRIPTION OF THE INVENTION

The bioreactor according to the invention has a dome-shaped culture vessel that rotates about its axis of symmetry set on a substantially horizontal plane. The circular ridge of the culture chamber is fluidtightly integrated with a gas-permeable membrane. The membrane-side of the culture chamber may be fluidtightly integrated with a rotating base in an orientation where the axis of symmetry of the dome-shaped culture chamber is substantially horizontal. The dome-shaped design and horizontal orientation provide a low shear environment and mass transfer that is favorable for culturing cells, particularly mammalian cells that form multicellular aggregates for the production of large biomasses.

For purposes of this invention, "dome-shaped," in the context of describing the culture vessel, means having the shape of a dome or cone, or a shape that substantially resembles a dome or cone. That is, the bottom of the vessel has a circular ridge, the vessel's axis of symmetry is perpendicular to the circular ridge and the walls of the vessel extend to an apex. The walls of the vessel leading to the apex are, for at least a portion, concave; the walls can have a partial non-curved portion. The apex can be a single point at the peak of the curved walls or can be a level surface at the peak of the curved walls. Several variations of the dome-shaped culture vessel are exemplified in FIGS. 1–3.

The term "substantially horizontal," in the context of describing the orientation of the axis of symmetry of the dome-shaped culture chamber, means that the axis is no more than 20 degrees from the horizontal plane. In a further preferred embodiment, the axis of symmetry is set no more than 10 degrees from the horizontal plane and, ideally, is in a horizontal plane.

Figure 1:
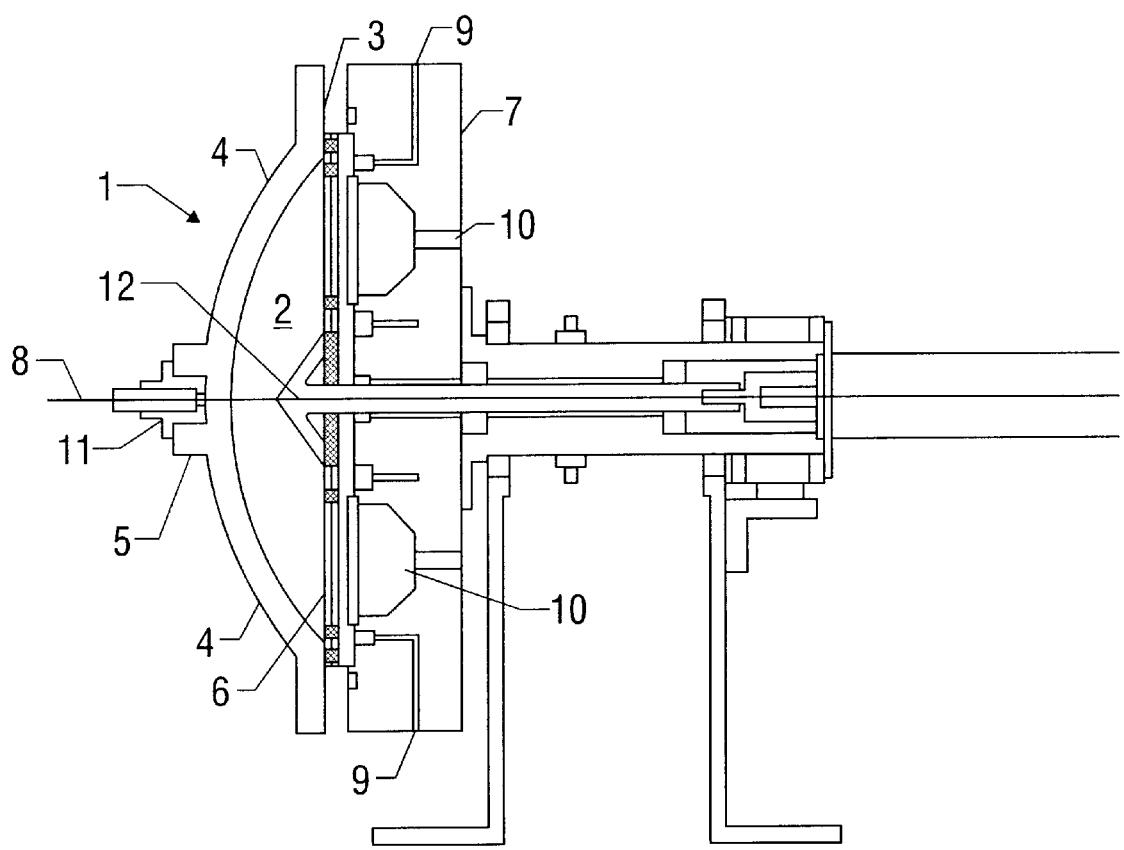
FIG. 1 is a schematic diagram a bioreactor having a dome-shaped culture vessel.

With reference to FIG. 1, the preferred embodiments of the bioreactor are described as follows. The inventive bioreactor comprises a dome-shaped culture chamber 1 having an interior volume 2, a bottom circular ridge 3, walls having at least a partially curved surface 4 and an apex 5. The circular ridge of the culture chamber is fluidtightly integrated with a gas-permeable membrane 6. The membrane-side of the culture chamber is fluidtightly integrated with a rotating base 7 in an orientation where the axis of symmetry of the dome-shaped culture chamber 8 is substantially horizontal.

Figure 2:
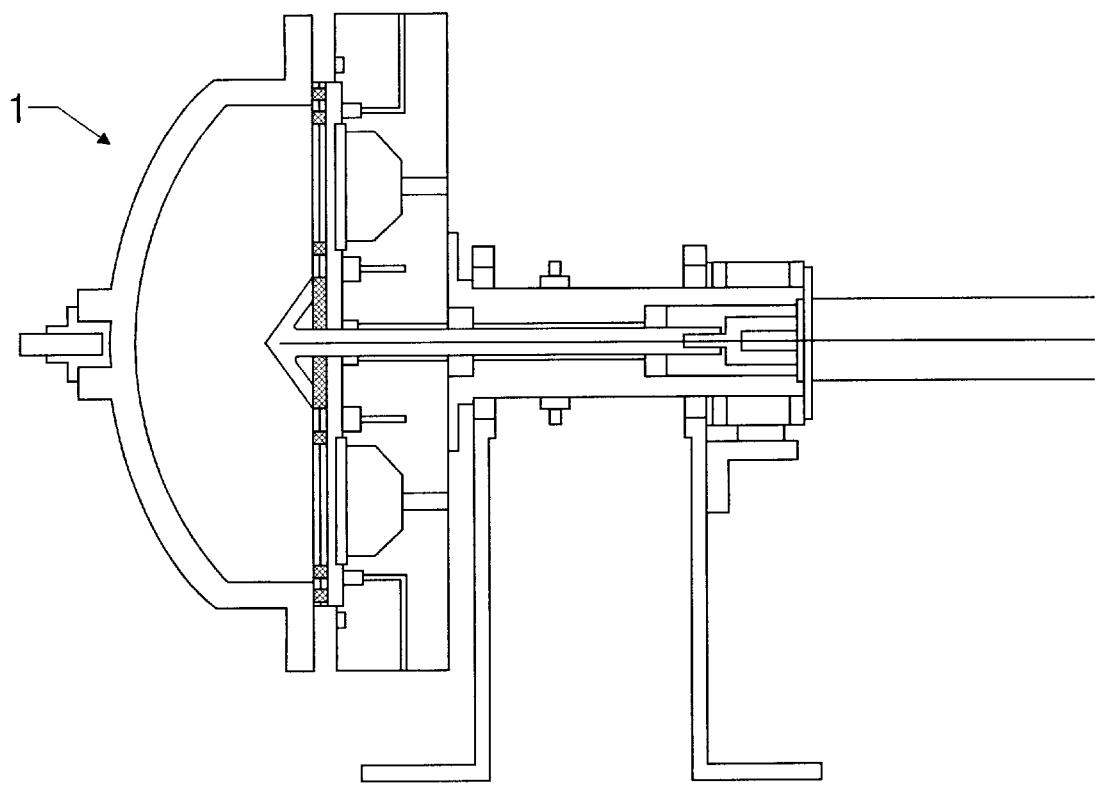
FIG. 2 is a schematic drawing of a bioreactor having a culture vessel with an alternative dome-shaped design.
Figure 3:
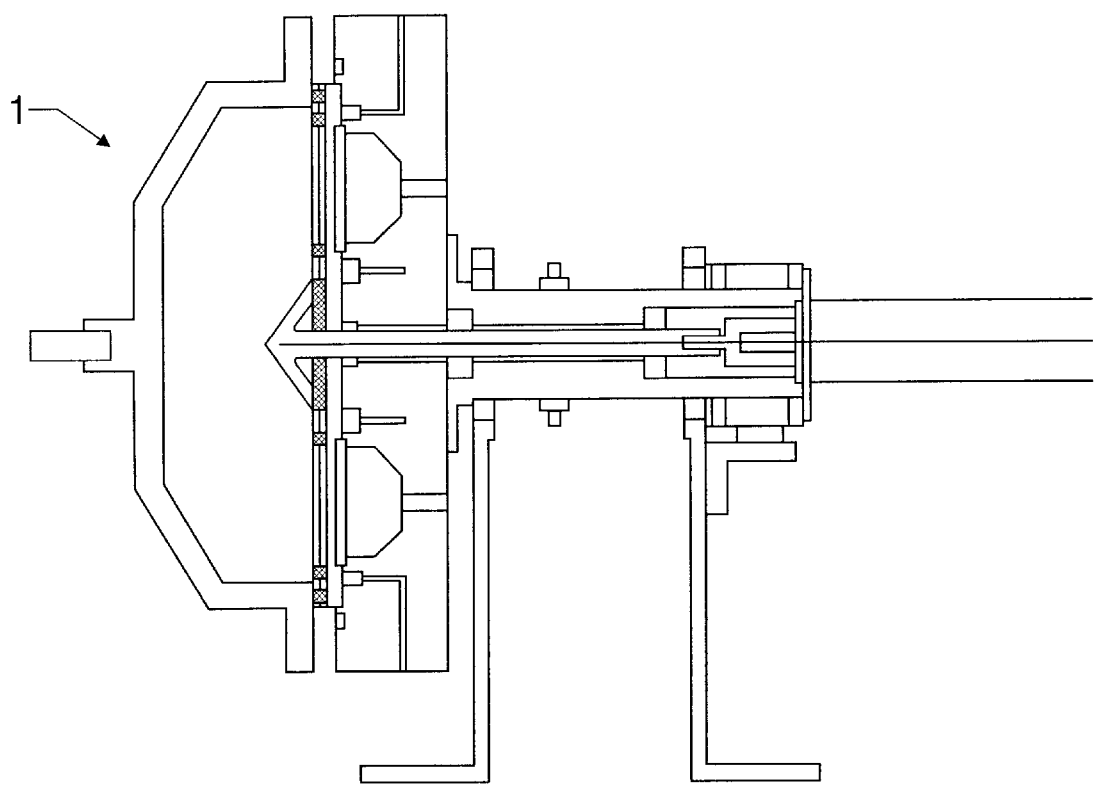
FIG. 3 is a schematic drawing of a bioreactor having a culture vessel with another alternative dome-shaped design.

The dome-shaped culture chamber can have a variety of shapes, as exemplified by the alternative dome-shapes depicted in FIGS. 1, 2, and 3. The culture chamber can be made of any material that is compatible with the culturing system, including glass, plastic, or stainless steel. Preferably, the vessel comprises a material that can be sterilized by ethylene oxide, gamma irradiation, or autoclaving, or, alternatively, is disposable.

The interior volume 2 of the culture vessel can vary greatly, depending upon the types of cells, amount of cells to be produced and available laboratory space. In a preferred embodiment, the volume of the substantially dome-shaped vessel is between about 10 mL and about 10 L. Small and medium scale laboratory cultures can preferably be performed in vessels of 100 mL, 250 mL, and 500 mL volumes. Larger preparative scale cultures can preferably be performed in vessels of 1 L, 5 L, and 10 L volumes.

The gas permeable material 3 can generally be any material compatible with the culturing system, ie., to allow flow of appropriate gases and to restrict flow of cells and liquid nutrients across the membrane. For example, the gas permeable membrane can comprise polytetrafluoroethylene, polyethylene, or porous hydrophobic TEFLON® membrane. The gas permeable membrane may additionally allow flow of liquids, nutrients, and metabolites across the membrane.

The bioreactor can further comprise an access port or a plurality of access ports to the culture vessel 9, 10, 11. The access ports allow transfer of materials and gases into and out of the bioreactor. Access ports can lead to the surface of the gas-permeable membrane 10 or can lead directly into the culture vessel 9, 11. The access ports leading directly into the culture vessel can go through the gas permeable membrane 9 or can go through the wall or apex of the culture vessel 11. The access ports can be any type of port used with culture or reaction vessels, including valves and membranes that can be penetrated by tubing, syringe, pipette or other sampling device.

The bioreactor can further comprise a agitator within the culture vessel 12. This agitator can be any type of device that provides additional agitation to the culture mixture, including a magnetic spinner or a mechanically driven propeller 12.

The invention is further directed to a method for culturing cells. The method according to the invention comprises providing the inventive bioreactor, adding cells and appropriate nutrients to the interior volume of the dome-shaped culture chamber, and rotating the base at a rate that generates suitable mass transfer and low shear stress. Where the mass transfer of the culture solution is provided by both the rotation of the culture chamber and by spinning an agitator in the culture vessel, the combined effects of these means must be weighed in determining the respective rotation rates.

The culturing of cells is preferably performed under conditions that optimize mass transfer and create low shear forces. Preferably, the culturing cells are subjected to average shear forces of less than about 1 dyne/cm$^2$, more preferably less than about 0.75 dyne/cm$^2$, and most preferably less than about 0.5 dyne/cm$^2$.

The bioreactor and culturing method according to the invention can be use for culturing any type of cell. In a preferred embodiment, the cells are eucaryotic cells, preferably mammalian cells. The cells can be adherent cells or non-adherent cells, single cells or multicellular aggregates. Adherent cells are attached to a substrate, such as microcarriers, fibrous supports or other cells.

The culturing method further comprise adding nutrients that enhance cell production and growth and removing waste products from the culturing process. Preferably, the gases are transferred across the gas permeable membrane 3. Alternatively, gases, nutrients or cell samples can be extracted from a port extending through the gas permeable membrane 9 or other access ports in the culture vessel wall or at its apex 11. For example, gas bubbles can be removed or culture fluid samples taken from an access port at the culture vessel apex to avoid disrupting the operation of the bioreactor. The culture vessel can be temporarily tilted to position the apex of the culture vessel so that bubbles rise to the apex access port.

EXAMPLE

A bioreactor can be designed with the following dimensions. The outer dome-shaped cell culture vessel has a radius of $r_o$=11 cm, radius of curvature r=8.6 cm and rotating at $w_o$ rpm, while the inner spinner has a radius of $r_i$=3 cm, height h=1 cm and rotates in the opposite direction at $w_i$ rpm. The rotating base has a perfluorocarbon chamber of 60 mL volume for oxygenation, nutrient inlet and outlet ports. The dome-shaped culture vessel of 125 mL volume is filled with culture medium into which aggregates of cells and microcarrier beads were introduced. The rates of rotation of the vessel and spinner are limited to a range in which the radial, circumferential, and axial velocity were large enough to suspend particles and provide adequate mixing, but small enough to prevent turbulence. Relative rotation rates may be determined and optimized by simulating flow fields with software such as FLUENT or FIDAP (both are commercially available from Fluent, Inc., Lebanon, N.H.). The unique advantage of this rotational perfuised hemispherical bioreactor is that the fluid shear force created by the differential rate of rotation of the dome and spinner would be more uniform and controllable.

TABLE 1

Alternative Bioreactor Dimensions

| Design | Inner Spinner rpm | Outer Dome rpm | Differential Rate[a] (rpm) | Outer Dome Radius | Inner Spinner Radius (cm) | Dome Height (cm) |
|---|---|---|---|---|---|---|
| 1 | 2 | −2 | 4 | 3.6 | 2.7 | 3.0 |
| 2 | 5 | −2 | 7 | 5.5 | 1.5 | 2.0 |
| 3 | 5 | −2 | 7 | 11 | 3 | 1.0 |

[a]The difference between the inner spinner and outer dome rotating rate.

The rates of rotation of the concave shaped vessel and spinner were limited to a range in which the radial, circumferential, and axial velocity were large enough to suspend particles and provide adequate mixing, but small enough to prevent turbulence. The unique advantage of this bioreactor was that the fluid shear force created by the differential rate of rotation of the dome and spinner would be more uniform and controllable.

All of the disclosed and claimed compositions, methods, and apparatus can be made and executed without undue experimentation in light of the present disclosure. While the compositions and methods of this invention have been described in terms of preferred embodiments, it will be apparent to those of skill in the art that variations can be applied to the compositions, methods, and apparatus and in the steps or in the sequence of steps of the methods described herein without departing from the concept, spirit and scope of the invention. More specifically, it will be apparent that certain agents which are both chemically and physiologically related can be substituted for the agents described herein while the same or similar results would be achieved. All such similar substitutes and modifications apparent to those skilled in the art are deemed to be within the spirit, scope and concept of the invention.

What is claimed is:

1. A bioreactor comprising:
    a dome-shaped culture vessel having rigid walls defining an interior volume, an apex, a bottom circular edge, and an axis of symmetry perpendicular to the bottom circular edge and running through the apex; and
    a gas-permeable membrane fluidtightly integrated with the bottom circular edge of the culture vessel, wherein the culture vessel is adapted to rotate about its axis of symmetry.

2. The bioreactor of claim 1, further comprising a rotating base fluidtightly integrated with the gas-permeable membrane, wherein the rotating base is fixed to rotate about the axis of symmetry of the dome-shaped culture vessel set on a substantially horizontal axis.

3. The bioreactor of claim 2, wherein the rotating base is attached to a horizontally disposed axle that is rotated by a motor.

4. The bioreactor of claim 2, wherein the rotating base comprises a plurality of access ports for transporting materials to and from the culture chamber.

5. The bioreactor of claim 1, wherein the culture vessel comprises an access port at its apex.

6. The bioreactor of claim 1, wherein the culture vessel contains an agitator.

7. The bioreactor of claim 6, wherein the agitator is a magnetic spinner or a mechanically driven propeller.

8. The bioreactor of claim 1, wherein the gas-permeable membrane comprises polytetrafluoroethylene, polyethylene, or porous hydrophobic TEFLON.

9. The bioreactor of claim 1, wherein the volume of the culture vessel between about 10 mL and about 10 L.

10. A method for culturing cells comprising:
   (a) providing a bioreactor, wherein the bioreactor comprises a dome-shaped culture vessel having rigid walls defining an interior volume, an apex, a bottom circular edge, and an axis of symmetry perpendicular to the bottom circular edge and running through the apex; and a gas-permeable membrane fluidtightly integrated with the bottom circular edge of the culture vessel; wherein the culture vessel is adapted to rotate about its axis of symmetry;
   (b) adding cells of interest to the culture vessel;
   (c) adding culture medium to the culture vessel;
   (d) rotating the rotating base at a rate sufficient to provide sufficient mass transfer and low shear forces on the culturing cells.

11. The method of claim 10, wherein:
   the bioreactor further comprises a rotating base fluidtightly integrated with the gas-permeable membrane; and
   the rotating base is fixed to rotate about the axis of symmetry of the dome-shaped culture vessel set on a substantially horizontal axis.

12. The method of claim 10, wherein the average shear force on the culturing cells is less than about 1 dyne/cm$^2$.

13. The method of claim 10, wherein the cells are eucaryotic cells.

14. The method of claim 13, wherein the eucaryotic cells are mammalian cells.

15. The method of claim 14, wherein the culturing cells are in the form of multicellular aggregates.

16. The method of claim 10, further comprising adding oxygen to the culture vessel through the gas permeable membrane.

17. The method of claim 10, further comprising providing a substrate to the culture vessel for the attachment of culturing cells.

18. The method of claim 17, wherein the substrate comprises microcarrier beads.

* * * * *

UNITED STATES PATENT AND TRADEMARK OFFICE
CERTIFICATE OF CORRECTION

PATENT NO.    :   6,001,642
DATED         :   December 14, 1999
INVENTOR(S)   :   Yow-Min D. Tsao It is certified that error appears in the above-identified patent and that said Letters Patent is hereby corrected as shown below:

Column 1, line 3, insert --The U.S. Government has a paid-up license in this invention and the right in limited circumstances to require the patent owner to license others on reasonable terms as provided for by the terms of NAS 9-97114 awarded by NASA.--

Column 1, line 31, delete "a" that occurs before "single".

Column 1, line 48, delete "N/M$^2$" and replace with --N/m$^2$--.

Column 2, line 48, delete "use" and replace with --uses--.

Column 3, line 22, insert --of-- after "diagram"

Column 4, line 55, delete "a" and replace with --an--.

Column 5, line 16, delete "use" and replace with --used--.

Column 5, line 63, delete "perfuised" and replace with --perfused--.

Signed and Sealed this

Fifteenth Day of August, 2000

*Attest:*

Q. TODD DICKINSON

*Attesting Officer*     *Director of Patents and Trademarks*